United States Patent [19]

Cremers et al.

[11] Patent Number: 4,925,307
[45] Date of Patent: * May 15, 1990

[54] APPARATUS AND METHOD FOR THE SPECTROCHEMICAL ANALYSIS OF LIQUIDS USING THE LASER SPARK

[75] Inventors: David A. Cremers, Los Alamos; Leon J. Radziemski, Las Cruces; Thomas R. Loree, Los Alamos, all of N. Mex.

[73] Assignee: The United States of America as represented by the United States Department of Energy, Washington, D.C.

[*] Notice: The portion of the term of this patent subsequent to Apr. 15, 2005 has been disclaimed.

[21] Appl. No.: 606,037

[22] Filed: May 1, 1984

[51] Int. Cl.$^5$ .................................... G01J 3/00
[52] U.S. Cl. ............................ 356/318; 356/319
[58] Field of Search ............... 356/317, 318, 301, 319, 356/323; 250/458.1, 461.2, 459.1

[56] References Cited

FOREIGN PATENT DOCUMENTS 0056239 7/1982 European Pat. Off. ............ 356/301

OTHER PUBLICATIONS

Prepmeier et al, "Q-Switched Laser Energy Absorption in the Plume of an Aluminum Aloy," Analyt. Chem. 41,700 (1969).
Hargis et al, "Multifrequency Laser Breakdown in SF$_6$," an abstract of a talk, 35th Annual Gaseous Elec. Conf., Oct. 19-22, 1982.
Cremers et al, "Direct Detection of Contaminants in Liquids via Laser Induced Breakdown Spectroscopy," 24th Rocky Mountain Conference, Denver, Colorado, Aug. 1-15, 1982 (published Jul. 15, 1982).

Primary Examiner—R. A. Rosenberger
Attorney, Agent, or Firm—Samuel M. Freund; Ray G. Wilson; Judson R. Hightower

[57] ABSTRACT

A method and apparatus for the qualitative and quantitative spectroscopic investigation of elements present in a liquid sample using the laser spark. A series of temporally closely spaced spark pairs is induced in the liquid sample utilizing pulsed electromagnetic radiation from a pair of lasers. The light pulses are not significantly absorbed by the sample so that the sparks occur inside of the liquid. The emitted light from the breakdown events is spectrally and temporally resolved, and the time period between the two laser pulses in each spark pair is adjusted to maximize the signal-to-noise ratio of the emitted signals. In comparison with the single pulse technique, a substantial reduction in the limits of detectability for many elements has been demonstrated. Narrowing of spectral features results in improved discrimination against interfering species.

22 Claims, 4 Drawing Sheets

APPARATUS AND METHOD FOR THE SPECTROCHEMICAL ANALYSIS OF LIQUIDS USING THE LASER SPARK

BACKGROUND OF THE INVENTION

The present invention relates generally to the qualitative and quantitative analysis of liquids and, more particularly, to the use of time resolved spectroscopic analysis of the emitted electromagnetic radiation from the liquid under investigation following two consecutive dielectric breakdown events therein caused to occur in the same volume.

Laser generated sparks in air have been used to detect the presence of atoms in vapors, aerosols, and particles. In the high temperatures of the spark plasma, material is reduced to elemental form and excited. Emitting species (ions, neutral atoms, and simple molecules) are identified by spectrally and temporally resolving the spark light.

Dielectric breakdown of pure water and several organic liquids occurs with focused laser pulse powers of $10^{10}$–$10^{11}$ W/cm$^2$. However, the breakdown threshold is influenced significantly by the presence of particles or dissolved materials. By contrast, breakdown of air occurs with power densities as low as $10^7$–$10^8$ W/cm$^2$. The higher laser pulse intensity requirements for producing dielectric breakdown in liquids can be met with commonly available lasers, rendering laser spark spectrometric analysis applicable to situations requiring a real-time and/or noninvasive analysis procedure. Real-time analysis is possible because the laser spark both prepares (vaporizes) and excites the sample. The technique is noninvasive in the sense that only optical access to and from the sampled medium is required. Laser sparks have been generated in liquids using 1–2 J pulses of 10–30 ns duration. Moreover, stable sparks can be produced using tightly focused laser pulses of 40–50 mJ at powers of about 3 MW, which is well within the specifications of reliable and small commercially available lasers which can operate at 10 to 20 Hz.

Mention of multiple laser pulses for time and spatially resolved spectrometric observations of laser generated plumes from the surface of a solid aluminum alloy appears in "Q-Switched Laser Energy Absorption in the Plume of an Aluminum Alloy," by E. H. Piepmeier and H. V. Malmstadt, Anal. Chem. 41, 701 (1969). Therein the authors discuss the investigation and modeling of such plumes and teach the use of time resolution and spatial resolution of laser spark emissions to separate sample spectra from spectra of the atmospheric species which surround the sample under investigation. The authors point out that a significant amount of laser energy is absorbed by the plume and therefore a multispike laser pulse would be a good way to further excite the sample species once they have entered the plume. Although this concept has similar motivation to the subject invention, no mention is made by Piepmeier et al. of any comparison in signal-to-noise characteristics with the results of a single spark at the surface of the object and multiple sparks within the laser induced plume. In fact, no observations are reported at the surface of the sample. The substantial absence of Al I species above the surface is only temporary, there being a transfer of atoms from the surface to points above the surface shortly after the spark occurs. This implies that atoms are being vaporized by the laser spark in significant numbers at the surface of the sample, many of them almost certainly in excited electronic states. Therefore Piepmeier et al. teaches away from the subject invention in that the analytical measurements are performed in the region of the laser generated plume with the intention of investigating its properties to improve laser sampling techniques rather than those of the surface at which the spark takes place. Our invention, on the other hand, teaches spark formation inside of a liquid and away from atmospheric presence so that the effects of such complications can be ignored. Moreover, substantial improvement in signal-to-noise ratio occurs, individual line widths narrow and line intensities increase when subsequent sparks are generated in the volume viewed in the subject invention over that resulting from the application of a single spark.

In "Multifrequency Laser Breakdown in SF$_6$," by P. J. Hargis, L. C. Pitchford, T. A. Green, J. R. Woodworth, and R. A. Hamil, an abstract of a talk presented at the 35th Annual Gaseous Electronics Conference, Dallas, Texas, October 19–22, 1982, the authors describe the application of two laser pulses of different wavelengths and coincident in space and time to a gaseous sample of SF$_6$ in order to enhance the intensity of the breakdown spark therein. The spectrum of the enhanced spark showed an increase in atomic fluorine emission. The wavelengths utilized in our invention do not significantly affect the measurements. The emission. Moreover, Hargis et al. do not mention time resolution of the electromagnetic emission, or the use of the multifrequency laser breakdown for analytical purposes. In fact, the emphasis of this work is for high voltage switching.

Use of laser-induced breakdown spectroscopy (LIBS) for detection of contaminants in liquids was described in a paper presented orally at the 24th Rocky Mountain Conference, Denver, Colorado, August 1–5, 1982 and the abstract therefor published on July 15, 1982. In the abstract for "Direct Detection of Contaminants in Liquids via Laser-Induced Breakdown Spectroscopy," by D. A. Cremers, L. J. Radziemski, and R. J. Martinez, the authors disclose the application of LIBS to liquid samples. However, no mention is made of the double spark technique of the instant invention.

Accordingly, an object of the subject invention is to significantly enhance the emission spectra of species excited by laser sparks in liquids over those obtained by conventional LIBS techniques.

Another object of our invention is to improve the detection limits of species in liquids over those obtainable by conventional LIBS techniques.

Yet another object of the instant invention is to monitor species in liquids which cannot be observed with the single spark LIBS technique.

Still another object of our invention is the resolution of closely spaced emission lines from species present in liquids following excitation by means of a laser spark.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the apparatus of this invention includes a first laser for generating pulsed electromagnetic radiation having sufficient intensity to produce optical dielectric breakdown in a volume of the liquid sample under investigation generating thereby excited atoms, molecules and ions characteristic of the liquid and, in particular, any substances in solution therein or otherwise carried thereby, a second laser for generating pulsed electromagnetic radiation which radiation is directed into the same breakdown volume after a first time period passes from the time of the dielectric breakdown caused by the pulsed electromagnetic radiation from the first laser, the electromagnetic radiation from the second laser having sufficient intensity to produce optical dielectric breakdown and to reexcite any of the already excited atoms, ions and molecules in the breakdown volume which have become de-excited during the first time period and to excite atoms, ions and molecules which were not fully excited by the first spark, producing thereby additional excited atoms, ions and molecules therein, whereby electromagnetic radiation is emitted from the additional excited atoms, molecules and ions and from the reexcited atoms, molecules and ions in the breakdown volume, the emitted electromagnetic radiation including continuum emission, discrete emission from the additional excited atoms, ions and molecules and discrete emission from the reexcited atoms, ions and molecules, and means for quantitatively detecting the discrete emission from one or more of the additional excited and reexcited atoms, ions and molecules after a second time period following the introduction of the pulsed electromagnetic radiation from the second laser to produce optical dielectric breakdown such that the continuum emission has substantially subsided, thereby maximizing the signal-to-noise ratio for the discrete emission from one or more of the additional excited and reexcited atoms, molecules and ions. Preferably, the emission from the additional excited and reexcited atoms, molecules and ions is spectrally resolved before entering the quantitative detective means. Preferably also, the pulsed electromagnetic radiation from the first and second lasers enter the liquid in a colinear manner.

In a further aspect of the present invention, in accordance with its objects and purposes, the method hereof includes causing a first dielectric breakdown to occur in the liquid sample under investigation generating thereby excited atoms, molecules and ions characteristic of the liquid sample, and particular, characteristic of its contents, waiting a first time period, then directing a first, pulsed high intensity laser radiation into the volume of the first dielectric breakdown causing thereby a second dielectric breakdown therein, whereby optimal additional energy is supplied to this volume thereby generating additional excited atoms, molecules and ions and reexciting said excited atoms, molecules and ions characteristic of the liquid and in particular, characteristic of its contents produced by the first dielectric breakdown which have become de-excited during the wait of the first time interval, whereby electromagnetic radiation is emitted which includes continuum emission, discrete emission from the reexcited atoms, ions and molecules, and discrete emission from the additional excited atoms, molecules and ions characteristic of the liquid and its contents, waiting a second time period, and then quantitatively detecting the discrete emission from any of the additional excited and reexcited atoms, molecules and ions, whereby the continuum emission has substantially subsided and the signal-to-background ratio of the emitted radiation from the additional excited and reexcited atoms, molecules and ions is maximized. Preferably, the first dielectric breakdown is caused using a second, pulsed high intensity laser radiation. However, it is within the scope of our invention that the first dielectric breakdown be produced by means such as electric sparks, for example. Preferably also, the quantitatively detecting step is preceded by a step of spectrally resolving the emitted discrete electromagnetic radiation from the additional excited and reexcited atoms, molecules and ions.

The subject invention, then, includes an apparatus and method for real-time in situ monitoring of liquid samples using multiple pairs of laser-induced breakdown events. The invention significantly improves existing repetitive single spark dielectric breakdown techniques such as conventional LIBS rendering observable species which cannot be observed under any conditions using that technique. Moreover, our invention improves the detectability over the single spark method as applied to liquids in that closely spaced emission lines can be resolved.

BRIEF DESCRIPTION OF THE DRAWINGS

The accompanying drawings, which are incorporated in and form a part of the specification, illustrate one embodiment of the present invention and, together with the description, serve to explain the principles of the invention. In the drawings.

DETAILED DESCRIPTION OF THE INVENTION

Figure 1:
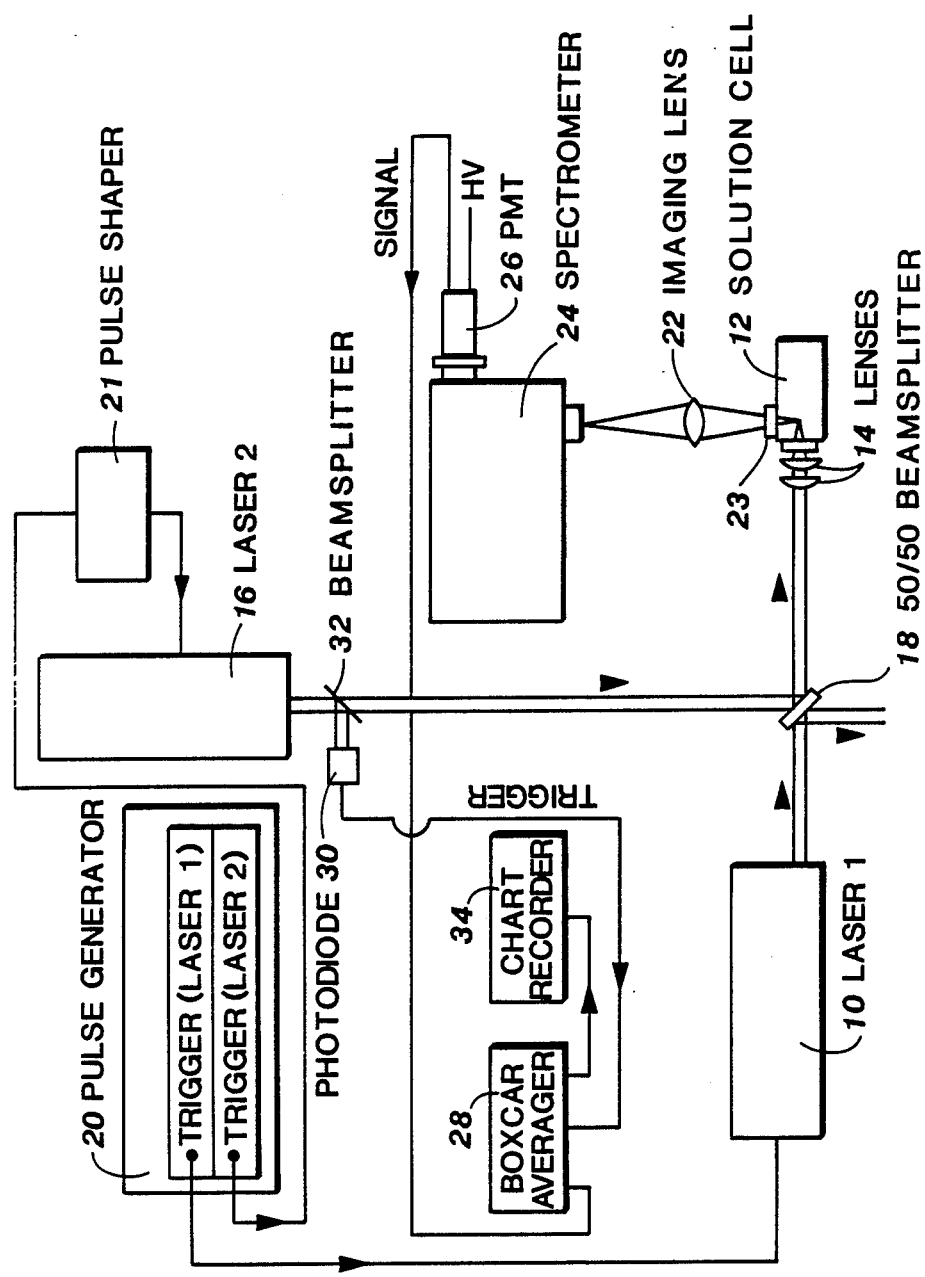
FIG. 1 shows a schematic representation of the apparatus of the subject invention.
Figure 2:
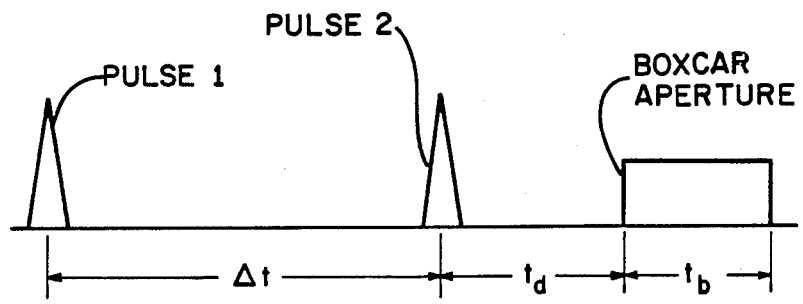
FIG. 2 shows the relative timing between the two laser pulses ($\Delta t$) and the signal observation delay time ($t_d$).

Reference will now be made in detail to the present preferred embodiment of the invention, an example of which is illustrated in the accompanying drawings. In the conventional laser-induced breakdown spectroscopy technique, a sufficiently energetic laser pulse is focused to generate a spark in the medium to be sampled. Material in the spark volume is vaporized, reduced to elemental form, and excited by the high temperature of the spark. Light emitted from the spark is spectrally resolved to identify the emitting species by means of their unique spectroscopic features. Time resolution of the emitted light generated by the spark event is used to reduce both spectral interferences and background. A boxcar averager is a convenient device to achieve the desired time resolution. That is, the aperture on the boxcar averager is adjusted to detect light from the spark only during a certain period after the laser pulse. Ordinarily, the emission signals from a plurality of sparks are averaged to increase the signal-to-noise ratio of the measurements.

According to the teachings of the subject invention, two temporally close, sequential laser sparks generated by two separate laser pulses are used to excite the same volume of a liquid sample. Typical separation times are approximately 20 $\mu$s. Principally, the emitted light from the second spark is analyzed, there being only a weak light intensity from the first spark produced approximately 20 $\mu$s earlier. The detection is performed in a similar manner to that described for a single spark hereinabove. A typical repetition rate for purposes of averaging the emissions from a series of closely spaced pulses is about 10 Hz. Significant enhancement of signals from emitting species is observed over the single repetitive spark method. For some species no detectable signal results from repetitive single spark event whereas a usable signal emerges using the technique of the instant invention.

As best understood by the inventors, a bubble is formed in the liquid by the spark produced by the first laser pulse. The bubble exists for hundreds of microseconds after the first spark has decayed. Located the bubble are neutral and ionized atoms and some simple molecules in the gas phase. Due to the greater density of the liquid sample compared with a gas, much of the energy of the first spark is used in vaporizing the liquid so that little energy remains to excite the vaporized material. This interpretation is supported by data which indicate that the temperature of the liquid spark is significantly lower than that of a spark in a gas. Once the bubble is formed, however, gaseous species are readily excited by the second laser spark. The resulting emission spectra of some species excited by the second spark are more intense and exhibit reduced line widths compared to species excited by a single spark; that is, the excitation characteristics more closely resemble those of a spark formed in a gas. Increased detectability of the atomic species is obtained by sampling the bubble with the second laser spark.

Turning now to the figures, FIG. 1 shows a schematic representation of the apparatus of the subject invention. Pulses of 1.06 $\mu$m radiation from a first Nd:YAG laser 10 are focused into a cell 12 containing the liquid under investigation by means of lenses 14. The volume of the cell was 20 cm$^3$ and it was constructed of Teflon ® to provide an inert environment. Each of the radiation pulses from the first laser is followed by a pulse of light from a second Nd:YAG laser 16 which pulses are also focused into the cell 12. The timing between the pulses was controlled to ±25 ns. Small, intense, reproducible sparks were obtained by focusing the pulses in the liquid within 2-5 mm of the input window. Physically longer but less reproducible sparks resulted from focusing the pulses further into the liquid away from the window. In a preferred embodiment of our invention the consecutive light pulses from the first and second lasers are first made colinear and then focused into the same volume of liquid using a beam splitter 18 and lenses 14. It was found to be impossible to obtain two sparks in the same focal volume with the pulses traveling through the liquid in opposite directions if they arrived at the liquid within some microseconds of one another since the spark produced by the first pulse prevented the second spark from forming. With the pulses arranged at right angles, bright flashes of light were frequently observed at the intersection of the focused beams instead of a reproducible spark. The flashes appeared to occur when bubbles formed by previous sparks passed through the focal volume. The colinear arrangement of the preferred embodiment was found to produce stable sparks. These sparks, however, were sensitive to the position of the beam splitter 18. The best alignment procedure was found to be the adjustment of the beam splitter to move the pulses from the second Nd:YAG laser 16 either vertically or horizontally until a steady spark was obtained with the beams overlapping. The dependence of the analyte signal upon the relative positions of the two sparks has not been investigated, but beam alignment did not have to be repeated more often than once every few days. The timing between the pairs of laser pulses and the relative timing of the pulses from the first laser and those from the second laser were controlled by a pulse generator 20. Pulse shaper 21 was used to better define the lasing time interval. Electromagnetic radiation emerging from the sparked liquid sample through a quartz window 23 at right angles to the path of the laser pulses was imaged by lens 22 into a spectrometer 24 where was it spectrally resolved and then detected by a photomultiplier tube 26. A boxcar averager 28, which is triggered by a signal from a photodiode 30, determined the temporal aperture of observation for the signal output from the photomultiplier tube 26. The photodiode 30 was responsive to radiation pulses from the second laser 16 which pulses are directed to it by means of a beam splitter 32. The signal from the photomultiplier tube is temporally resolved and averaged over many sparks by the boxcar averager. The width of the boxcar aperture ($t_b$) and the time between the formation of the second spark and the opening of the aperture ($t_d$) were adjusted to view particular events during spark decay. Emission intensity data were obtained by scanning the spectrometer wavelength over emission features and recording the boxcar-processed signal on a chart recorder 34. It should be mentioned at this point that any laser wavelengths which are substantially transmitted by the liquid sample can be used for the analysis of the subject invention. The Table describes typical apparatus settings.

The timing sequence for a pulse from the first laser and one from the second laser ($\Delta t$) and the beginning of

TABLE

A. Lasers

| | | |
|---|---|---|
| 1. | Laser 1 | Nd:YAG |
| | pulsewidth | 15 ns |
| | energy | 30–70 mJ/pulse |
| | repetition rate | 10 Hz |
| | wavelength | 1064 nm |
| 2. | Laser 2 | Nd:YAG |
| | pulse width | 15 ns |
| | energy | 125 mJ/pulse (fixed) |
| | repetition rate | 10 Hz |
| | wavelength | 1064 nm |

B. Detection System

| | | |
|---|---|---|
| 1. | Spectrometer | 0.5 m Czerny-Turner |
| | gratings | 1200 l/mm, 500 nm blaze |
| | | 3600 l/mm, 300 nm blaze |
| | slit widths | 10–200 μm |
| | slit height | 2 cm |
| | spectral order | first |
| | order filters | glass for 360 nm < λ < 600 nm |
| | | Corning CS 3-71 for λ > 600 nm |
| 2. | Photomultiplier | |
| | Signal Processing | |
| | Boxcar Averager | 60–5000 ns |
| | aperture delay | |
| | aperture duration | 30–1000 ns |
| | output time constant | 0.1 s |
| | scan select | not used |
| | trigger | external, signal supplied by photodiode monitoring laser output, + slope, + level | the boxcar averaging period ($t_b$) after the pulse from the second laser ($t_d$) is schematically shown in Figure.

Figure 3:
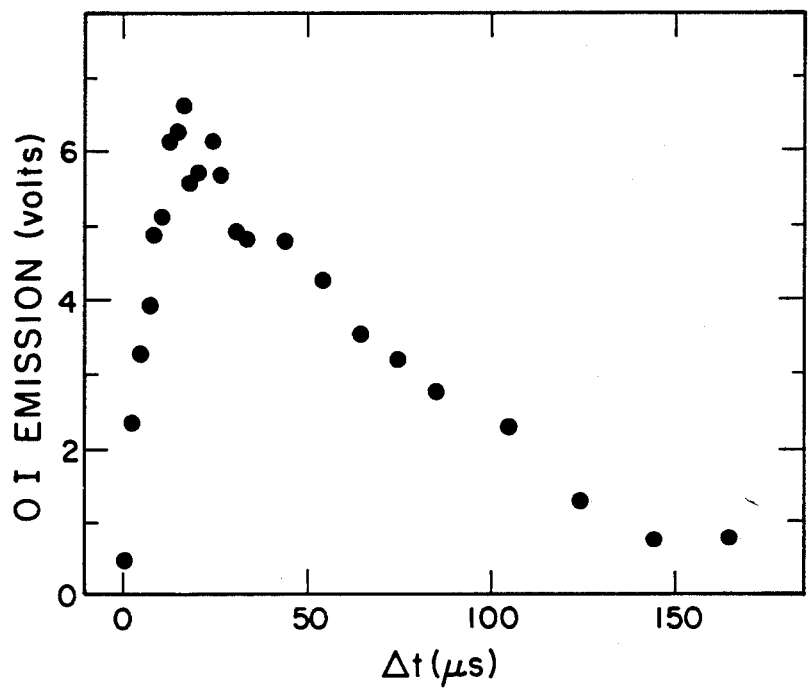
FIG. 3 shows the variation of O I emission with $\Delta t$.

FIG. 3 shows the effect on the emission intensity from oxygen atoms of varying the time between the pulses ($\Delta t$) in a pulse pair. With a single spark in deionized water, a very weak emission was observed from the intense O I (oxygen neutral atom) spectroscopic feature at 777.4 nm using a delay time, $t_d$ of 50 ns, which is sufficient to insure that the background continuum has substantially disappeared. The O I signal strength increased by a factor of about 50 using the double spark procedure of the subject invention. It is seen that the maximum O I emission occurs at $\Delta t = 18$ μs and then decreases slowly with increasing $\Delta t$. Moreover, with a single spark in deionized water, emission from H I at 656.3 nm was not observed under any conditions although a signal of 200 mV could have been detected given the observed magnitude of the background noise. However, with the double spark procedure, $t_d = 60$ ns and $\Delta t = 18$ μs, an H I emission signal of 28 V was measured corresponding to an enhancement of at least 140. Emissions from H I and O I were observed as long as 500 ns ($t_d$) after the pulse from the second laser.

Figure 4:
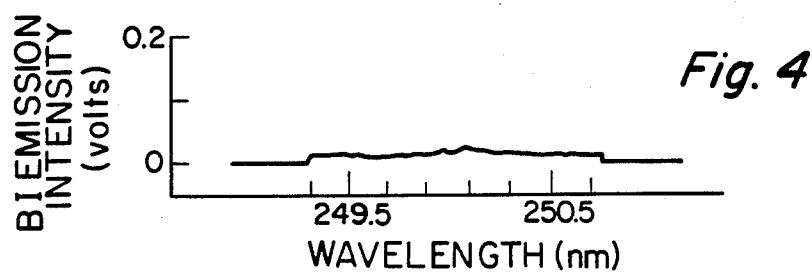
FIG. 4 shows a scan over the partial spectrum of B I where features centered at 249.68 and 249.77 nm are known to be located, the liquid sample containing boron excited by only the first of two lasers used in the double spark procedure of the instant invention.
Figure 5:
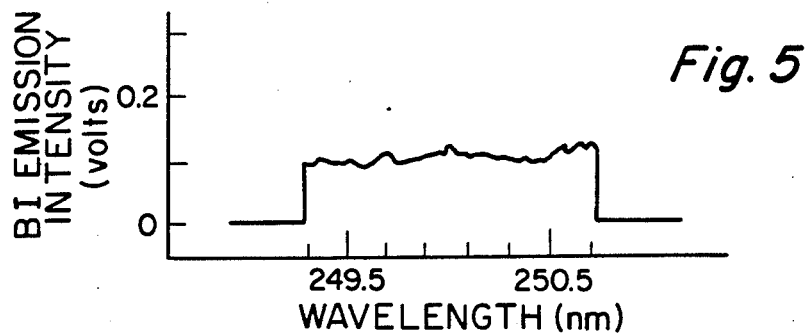
FIG. 5 shows a scan over the partial spectrum of B I where features centered at 249.68 and 249.77 nm are known to be located, the liquid sample containing boron excited by only the second of two lasers used in the double spark procedure of the instant invention.
Figure 6:
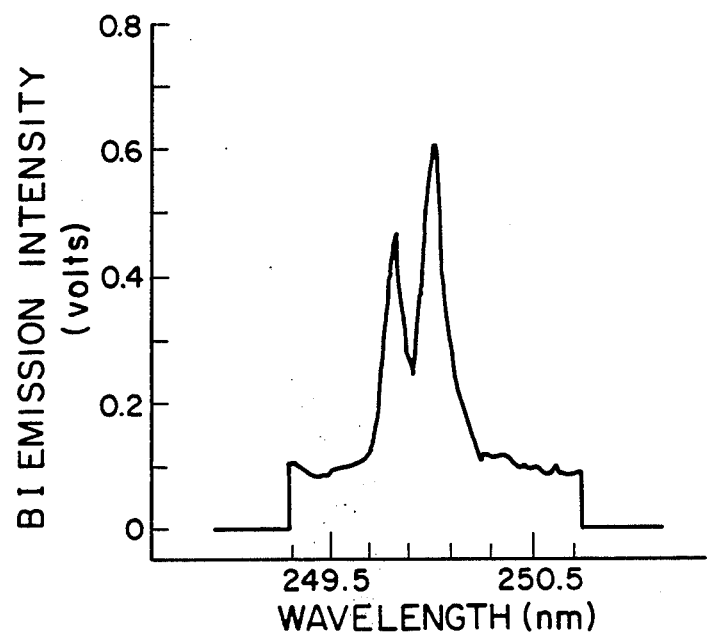
FIG. 6 shows a partial spectrum of B I in the same wavelength region as FIGS. 4 and 5, obtained using both lasers as taught in the subject invention.

In addition to the major species of hydrogen and oxygen the double spark procedure enhanced emissions from species present in trace amounts in aqueous solutions. FIG. 4 shows a scan over the spectroscopic locations of emission lines from B I at 249.68 and 249.77 nm for a solution of 5000 μg/cc boron/H$_2$O when only light pulses from laser 1 10 are applied to the sample. A small background level is seen to be present, but no boron signal was observed. A greater background level was observed with light pulses only from laser 2 16 causing sparks in the sample, but again no positive identification of boron emission could be made. This situation is illustrated in FIG. 5. With both lasers operating, however, emission from the pair of boron lines was clearly observed as is illustrated in FIG. 6. The detection limit of boron in water was significantly reduced using the method and apparatus of the instant invention. Limits of detection for boron using both the single spark procedure and our invention were determined by measuring the B I signal near 249.7 nm at each concentration first with one laser and then with two lasers operating to minimize variations in experimental conditions. The noise levels obtained from 16 replicate measurements of the B I signal in both cases were comparable. Boron detection limits for the single spark procedure and the spark pair procedure were found to be 1200 and 80 μg/cc, respectively, representing a 15-fold increase in detection sensitivity using our invention. Similar results were obtained for other elements such as Be, which are not readily observed in liquids with the single spark procedure. For the elements Ca and Mg, which are detectable at levels higher than 1 μg/cc with the single spark technique the double spark technique of our invention resulted in signal enhancements of factors of 3 or 4, whereas only factors of 2 enhancements were obtained for species such as Li and Na which are detectable at much lower levels (about 0.01 μg/cc) with the single spark method. Applicants believe that this result derives from the possibility that the conditions produced by the single spark are sufficient to fully excite the alkali metals, which are characterized by low lying energy levels. The instant invention was also used to generate emissions from O I, H I and C I (247.9 nm) in pure methanol which were unobservable using a single spark.

Figure 7:
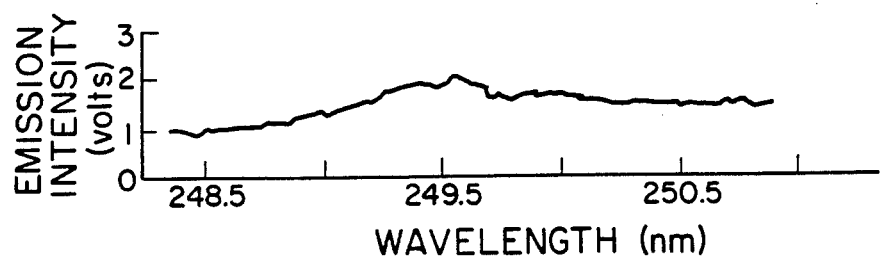
FIG. 7 shows a scan over the partial spectrum of Be I where a set of three features centered at 249.46 nm are known to be located, the liquid sample containing beryllium excited by only the second of two lasers used in the double spark procedure of the instant invention.
Figure 8:
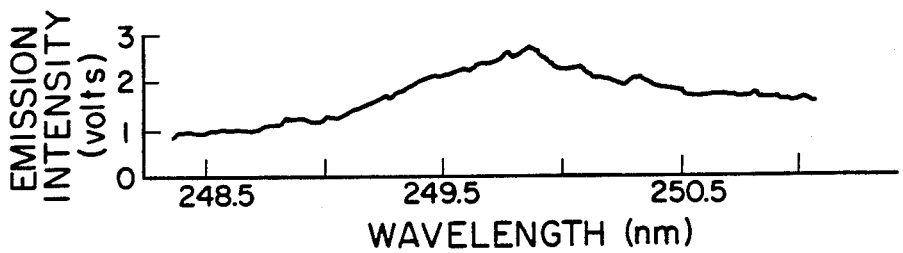
FIG. 8 shows a scan over the partial spectrum of B I and Be I where features centered at 249.68 and 249.77 nm due to B I and a set of these features centered at 249.46 nm due to Be I are known to be located, the liquid sample containing boron and beryllium excited by only the second of two lasers used in the double spark procedure of the instant invention.
Figure 9:
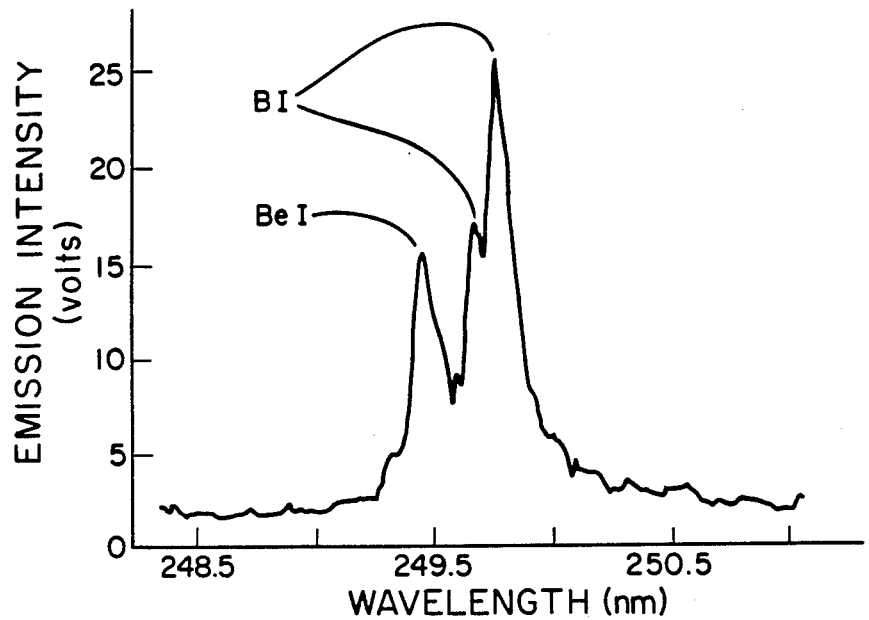
FIG. 9 shows a partial spectrum of Be I and B I in the same wavelength region as described in FIGS. 7 and 8, obtained using the two spark procedure of the subject invention applied to the same liquid containing the two elements examined in FIG. 8 hereof.

It was also found that the width of some spectral features is reduced using the two spark procedure. This unexpected property is useful for resolving closely spaced emission lines which are broadened in the single water spark to where they interfere with adjacent lines. FIG. 7 shows a scan over the wavelength region where a set of three lines from Be I are known to be centered at 249.46 nm obtained using a series of single sparks applied to a water solution having beryllium as a trace element. Beryllium/H$_2$O concentration was 2000 μg/cc. FIG. 8 shows a scan over the wavelength region where a doublet from B I is known to be found at 249.68 nm and 249.77 nm and a set of three lines from Be I are known to be centered at 249.46 nm obtained using a series of single sparks applied to a water solution having boron and beryllium as trace elements. The beryllium/H$_2$O and boron/H$_2$O concentrations were both 2000 μg/cc. To be observed from FIGS. 7 and 8 is that emission from the two atomic species overlap and would prevent identification of either species in an analytical procedure based on the single spark. With our invention, however, the lines sharpened so that when the same aqueous solution used in FIG. 8 containing both elements at 2000 μg/cc is analyzed using a plurality of spark pairs according to our invention, both elements were readily observed as shown in FIG. 9. The instrumental resolution of 0.3 nm prevented the individual Be I lines from being resolved.

Nonaqueous solutions of lithium were investigated by the one spark and spark pair procedures. The 670.8 nm Li I emission feature was monitored from methanol, ethanol and acetone solutions containing about 1.4 μg/cc of lithium. The Li I emission signals from the 3 solutions were of approximately equal intensity and were 2 to 4 times larger than the signal from a 1.4 μg/cc solution of lithium in water. It is believed by the inventors that this difference is related to the greater values for the boiling point, heat capacity, and heat of vaporization of water compared to the organic solvents investigated; that is, for a given laser pulse energy, larger volumes of the organic solvents are vaporized compared to water. Therefore, greater numbers of Li atoms are excited in the organic media. Signal enhancements of the order of two to five were obtained for the Li I emission signal in nonaqueous solvents using the spark pair procedure of the instant invention which is slightly greater than the enhancements obtained for Li in aqueous solution. As mentioned hereinabove, emissions from C I, O I and H I were observed from pure methanol only by using the double spark procedure.

The use of the laser spark to analyze flowing samples was investigated using the single spark procedure. No difference in either signal or noise has been observed between the flow on or off condition. It is expected that this result would obtain for the double spark technique.

Occassionally, the maximum intensity for the emissions from the additional excited and reexcited atoms, molecules and ions will occur at different times. Under those circumstances, temporal resolution might be utilized to maximize the signal-to-background ratio of the atomic emission, for example, by selecting an observation time interval where substantial interferences from one or more of the ionic and molecular emissions would be minimized.

The instant invention, then, represents a substantial improvement over the known single spark technique. The repetitive spark pair procedure of our invention increases the signal strength of emissions from elements in liquid samples undergoing laser breakdown and simultaneously reduces the line width of the emission features such that a significant reduction in the detectable limit for these events occurs along with an improved ability to discriminate against interfering spectra.

The foregoing description of a preferred embodiment of the invention has been presented for purposes of illustration and description. It is not intended to be exhaustive or to limit the invention to the precise form disclosed, and obviously many modifications and variations are possible in light of the above teaching. For example, the first spark of the spark pair can be generated using conventional electrodes, and the second spark by high intensity laser radiation.

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. An apparatus for the spectrochemical analysis of a liquid, which comprises in combination:
    a. a first laser for generating a first pulsed electromagnetic radiation having sufficient intensity to produce optical dielectric breakdown in a volume of the liquid under investigation generating thereby excited atoms, molecules and ions characteristic of the liquid;
    b. a second laser for generating a second pulsed electromagnetic radiation, said second pulsed electromagnetic radiation being directed into said breakdown volume after the elapse of a first time period after said first optical dielectric breakdown, said second pulsed electromagnetic radiation having sufficient intensity to produce a second optical dielectric breakdown in order to reexcite said excited atoms, molecules and ions in said breakdown volume which have become de-excited during said first time period, and to produce additional excited atoms, molecules and ions therein, whereby electromagnetic radiation is emitted from said breakdown volume, said electromagnetic radiation including continuum emission, discrete emission from said additional excited atoms, molecules and ions, and discrete emission from said reexcited atoms, molecules and ions; and
    c. means for quantitatively detecting said discrete emitted electromagnetic radiation from at least one of said additional excited atoms, ions and molecules, and from at least one of said reexcited atoms, ions and molecules after a second time period, whereby sufficient time has elapsed following said second, pulsed electromagnetic radiation for said continuum emission to substantially subside, thereby permitting the signal-to-background ratio for said discrete electromagnetic radiation emission from at least one of said additional excited atoms, ions and molecules, and from at least one of said reexcited atoms, ions and molecules to become substantially maximized.

2. The apparatus as described in claim 1, wherein means are provided for spectrally resolving said emitted discrete electromagnetic radiation from said additional excited atoms, ions and molecules and from said reexcited atoms, ions and molecules before detection of said discrete electromagnetic radiation from at least one of said excited atoms, molecules and ions and said reexcited atoms, molecules and ions is performed by said detecting means.

3. The apparatus as described in claim 2, wherein means are provided for directing said first pulsed electromagnetic radiation and said second pulsed electromagnetic radiation into the liquid in a substantially colinear manner.

4. The apparatus as described in claim 3, wherein means are provided for repetitively applying said first pulsed electromagnetic radiation and said second pulsed electromagnetic radiation to the liquid, each of said repetitive applications occurring after the elapse of a third time period whereby said breakdown volume is substantially clear of bubbles formed by previous said optical dielectric breakdown events, and wherein means are provided for processing a plurality of signals derived from said detecting means having responded to said repetitive application of said first pulsed electromagnetic radiation and said second pulsed electromagnetic radiation a plurality of times, thereby improving the signal-to-noise ratio of the data obtained by said detecting means.

5. The apparatus as described in claim 4, wherein means are provided to flow the liquid thereby providing a new sample for each of said repetitive applications of said first pulsed electromagnetic radiation and said second pulsed electromagnetic radiation to the liquid.

6. The apparatus as described in claim 5, wherein said first time period is approximately 18 $\mu$s and said second time period is about 60 ns.

7. The apparatus as described in claim 4, wherein said third time period is greater that approximately 0.1 s.

8. A method for the spectrochemical analysis of a liquid, which comprises the steps of:

a. causing a first dielectric breakdown to occur in the liquid generating thereby excited atoms, molecules and ions characteristic of the liquid;
b. waiting a first time period;
c. directing a first, pulsed high intensity laser radiation into the volume of said first dielectric breakdown after said first time period, thereby causing a second dielectric breakdown therein, whereby substantially optimal additional energy is supplied to said volume thereby generating additional excited atoms, molecules and ions and reexciting those of said excited atoms, molecules, and ions characteristic of the liquid produced by said first dielectric breakdown which have become de-excited during said first time period, whereby electromagnetic radiation is emitted, said electromagnetic radiation including continuum emission, discrete emission from said additional excited atoms, molecules and ions, and discrete emission from said reexcited atoms, molecules and ions;
d. waiting a second time period; and
e. quantitatively detecting said discrete emitted electromagnetic radiation from said additional excited atoms, ions and molecules and from said reexcited atoms, ions and molecules after said second time period, whereby said continuum emission has substantially subsided and the signal-to-background ratio of said emitted discrete electromagnetic radiation from at least one of said additional excited atoms, ions and molecules and said reexcited atoms, ions and molecules, is substantially maximized relative to any interfering emitted discrete electromagnetic radiation from said additional excited ions, atoms and molecules and from said reexcited atoms, ions and molecules.

9. The method as described in claim 8, wherein said first dielectric breakdown is caused using a second, pulsed high intensity radiation.

10. The method as described in claim 9, wherein said quantitatively detecting step is preceded by a step of spectrally resolving said emitted discrete electromagnetic radiation from said additional excited atoms, ions and molecules and from said reexcited atoms, ions and molecules.

11. The method as described in claim 10, wherein the liquid is caused to flow through said volume of said first dielectric breakdown.

12. The method as described in claim 11, wherein said first time period is approximately 18 $\mu$s and said second time period is about 60 ns.

13. The method as described in claim 10, wherein steps a–e are repeated a plurality of times at a rate of repetition which permits said volume of said first dielectric breakdown to be substantially clear of bubbles formed by previous dielectric breakdown events, and wherein the results of said quantitatively detecting step are averaged thereby producing an improved signal-to-noise ratio for said quantitatively detected emitted electromagnetic radiation from said additional excited atoms, ions and molecules and from said reexcited atoms, ions and molecules, said method further including using a second, pulsed high intensity radiation to cause said first dielectric breakdown, and preceding said quantitatively detecting step by a step for resolving said emitted discrete electromagnetic radiation from said additional excited atoms, ions and molecules and from said reexcited atoms, ions and molecules.

14. The method as described in claim 13, wherein the liquid is caused to flow through said volume of said first dielectric breakdown.

15. The method as described in claim 14, wherein said first time period is approximately 18 $\mu$s and said second time period is about 60 ns.

16. An apparatus for the spectrochemical analysis of a liquid, which comprises in combination:
a. a first laser for generating a first pulsed electromagnetic radiation having sufficient intensity to produce optical dielectric breakdown in a volume of the liquid under investigation generating thereby excited atoms, molecules and ions characteristic of the liquid;
b. a second laser for generating a second pulsed electromagnetic radiation, said second pulsed electromagnetic radiation being directed into said breakdown volume after the elapse of a first time period after said first optical dielectric breakdown, said second pulsed electromagnetic radiation having sufficient intensity to produce a second optical dielectric breakdown in order to reexcite said excited atoms, molecules and ions in said breakdown volume which have become de-excited during said first time period, and to produce additional excited atoms, molecules and ions therein, whereby electromagnetic radiation is emitted from said breakdown volume, said electromagnetic radiation including continuum emission, discrete emission from said additional excited atoms, ions and molecules, and discrete emission from said reexcited atoms, ions and molecules; and
c. means for quantitatively detecting said discrete emitted electromagnetic radiation from said additional excited atoms and from said reexcited atoms after a second time period, whereby sufficient time has elapsed following said second, pulsed electromagnetic radiation for said continuum emission to substantially subside, for any of said discrete emission from said additional excited ions and molecules and from said reexcited ions and molecules which interferes with said detecting means for detecting said discrete electromagnetic radiation emitted from said additional excited atoms and from said reexcited atoms to substantially subside, and for the signal-to-background ratio for said discrete electromagnetic radiation emission from said additional excited atoms and from said reexcited atoms to become substantially maximized.

17. A method for the spectrochemical analysis of a liquid, which comprises the steps of:
a. directing a first, pulsed high intensity laser radiation into said volume thereby causing a first optical dielectric breakdown to occur in the liquid generating thereby excited atoms, molecules and ions characteristic of the liquid and of its contents;
b. waiting a first time period;
c. directing a second, pulsed high intensity laser radiation into said volume of said first dielectric breakdown after said first time period, thereby causing a second dielectric breakdown therein, whereby substantially optimal additional energy is supplied to said volume thereby generating additional excited atoms, molecules and ions and reexciting those of said excited atoms, molecules, and ions characteristic of the liquid and its contents produced by said first dielectric breakdown which have become de-excited during said first time period, whereby electromagnetic radiation is emitted, said electromagnetic radiation including continuum emission, discrete emission from said additional excited atoms, molecules and ions, and from said reexcited atoms, molecules and ions;

d. waiting a second time period; and e. quantitatively detecting said discrete emitted electromagnetic radiation from said additional excited atoms and from said reexcited atoms after said second time period, whereby said continuum emission has substantially subsided and the signal-to-background ratio of said emitted discrete electromagnetic radiation from said additional excited atoms and from said reexcited atoms is substantially maximized relative to any interfering emitted discrete electromagnetic radiation from said additional excited molecules and ions and from said reexcited molecules and ions.

18. An apparatus for the spectrochemical analysis of a liquid, which comprises in combination:

a. a laser for generating a first pulsed electromagnetic radiation and a second pulsed electromagnetic radiation, said first pulsed electromagnetic radiation having sufficient intensity to produce optical dielectric breakdown in a volume of the liquid under investigation generating thereby excited atoms, molecules and ions characteristic of the liquid, said second pulsed electromagnetic radiation being directed into said breakdown volume after the elapse of a first time period after said first optical dielectric breakdown, said second pulsed electromagnetic radiation having sufficient intensity to produce a second optical dielectric breakdown in order to reexcite said excited atoms, molecules and ions in said breakdown volume which have become de-excited during said first time period, and to produce additional excited atoms, molecules and ions therein, whereby electromagnetic radiation is emitted from said breakdown volume, said electromagnetic radiation including continuum emission, discrete emission from said additional excited atoms, molecules and ions, and discrete emission from said reexcited atoms, molecules and ions; and b. means for quantitatively detecting said discrete emitted electromagnetic radiation from at least one of said additional excited atoms, ions and molecules, and from at least one of said reexcited atoms, ions and molecules after a second time period, whereby sufficient time has elapsed following said second, pulsed electromagnetic radiation for said continuum emission to substantially subside, thereby permitting the signal-to-background ratio for said discrete electromagnetic radiation emission from at least one of said additional excited atoms, ions and molecules, and from at least one of said reexcited atoms, ions and molecules to become substantially maximized.

19. The apparatus as described in claim 18, wherein means are provided for spectrally resolving said emitted discrete electromagnetic radiation from said additional excited atoms, ions and molecules and from said reexcited atoms, ions and molecules before detection of said discrete electromagnetic radiation from at least one of said additional excited atoms, molecules and ions and said reexcited atoms, molecules and ions is performed by said detecting means.

20. The apparatus as described in claim 19, wherein said first time period is approximately 18 $\mu$s and said second time period is about 60 ns.

21. A method for the spectrochemical analysis of a liquid, which comprises the steps of:

a. directing a first pulse of high intensity laser radiation into a volume of the liquid causing thereby a first dielectric breakdown to occur in the liquid generating thereby excited atoms, molecules and ions characteristic of the liquid;

b. waiting a first time period;

c. directing a second pulse of high intensity laser radiation into the said volume of said first dielectric breakdown after said first time period, thereby causing a second dielectric breakdown therein, whereby substantially optimal additional energy is supplied to said volume thereby generating additional excited atoms, molecules and ions and reexciting those of said excited atoms, molecules, and ions characteristic of the liquid produced by said first dielectric breakdown which have become de-excited during said first time period, whereby electromagnetic radiation is emitted, said electromagnetic radiation including continuum emission, discrete emission from said additional excited atoms, molecules and ions, and discrete emission from said reexcited atoms, molecules and ions;

d. waiting a second time period; and e. quantitatively detecting said discrete emitted electromagnetic radiation from said additional excited atoms, ions and molecules and from said reexcited atoms, ions and molecules after said second time period, whereby said continuum emission has substantially subsided and the signal-to-background ratio of said emitted discrete electromagnetic radiation from at least one of said additional excited atoms, ions and molecules and said reexcited atoms, ions and molecules, is substantially maximized relative to any interfering emitted discrete electromagnetic radiation from said additional excited atoms, ions and molecules and from said reexcited atoms, ions and molecules.

22. The method as described in claim 21, wherein said quantitatively detecting step is preceded by a step of spectrally resolving said emitted discrete electromagnetic radiation from said additional excited atoms, ions and molecules and from said reexcited atoms, ions and molecules.

* * * * *